Figure 1:
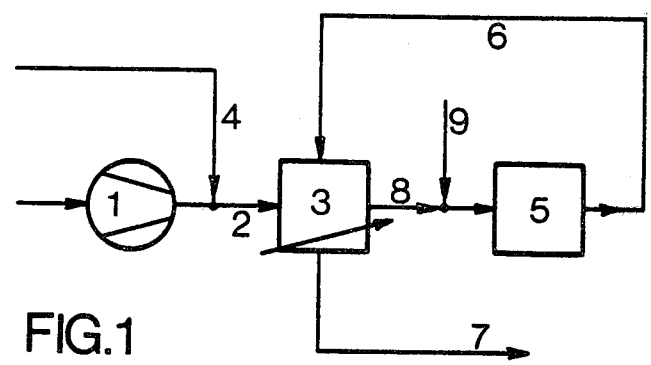

United States Patent [19]

Stockburger et al.

[11] 4,369,327

[45] Jan. 18, 1983

[54] PREPARATION OF PHTHALIC ANHYDRIDE

[75] Inventors: Dieter Stockburger; Wilhelm Schultz, both of Gruenstadt; Johannes E. Schmidt; Friedrich Wirth, both of Ludwigshafen; Herwig Hoffmann, Frankenthal; Bernhard Holzknecht, Ellerstadt; Klaus Wintermantel, Weinheim-Oberflockenbach, all of Fed. Rep. of Germany

[73] Assignee: BASF Aktiengesellschaft, Ludwigshafen, Fed. Rep. of Germany

[21] Appl. No.: 313,177

[22] Filed: Oct. 20, 1981

[30] Foreign Application Priority Data

Nov. 26, 1980 [DE] Fed. Rep. of Germany ....... 3044518

[51] Int. Cl.³ .......................................... C07D 307/89
[52] U.S. Cl. .................................... 549/248; 549/249
[58] Field of Search ......................... 260/346.4, 346.7; 549/248, 249

[56] References Cited

U.S. PATENT DOCUMENTS

| 3,248,453 | 4/1966 | Beyrard | 260/346.4 |
| 3,535,345 | 10/1970 | Egbert | 260/346.4 |
| 3,869,479 | 3/1975 | Barth et al. | 260/346.4 |
| 4,119,645 | 10/1978 | Auroy et al. | 260/346.4 |
| 4,169,098 | 9/1979 | Hellmer et al. | 260/346.4 |
| 4,252,772 | 2/1981 | Way | 260/346.7 X |
| 4,269,776 | 5/1981 | Keunecke et al. | 260/346.4 |

*Primary Examiner*—Richard Raymond
*Attorney, Agent, or Firm*—John H. Shurtleff

[57] ABSTRACT

A process for the preparation of phthalic anhydride (PA) of catalytic oxidation of naphthalene or o-xylene with air, a preheated mixture of air and naphthalene or o-xylene being passed into a reactor charged with the catalyst, and the reaction gas leaving the reactor being passed through a separator in which the PA is separated out as a solid, in which process the air fed to the reactor is preheated, before or after the admixture of naphthalene or of o-xylene, by using it to cool the reaction gas in the PA separator.

6 Claims, 2 Drawing Figures

PREPARATION OF PHTHALIC ANHYDRIDE

The present invention relates to a process for the preparation of phthalic anhydride (PA) by catalytic oxidation of naphthalene or o-xylene with air.

PA is manufactured industrially by catalytic gas oxidation of naphthalene or o-xylene with air. In this known process, the o-xylene is injected into compressed and preheated air, or the compressed and preheated air is charged with naphthalene vapor and the resulting vaporous mixture, which is at from about 130° to 190° C., is passed through a reactor, charged with the catalyst, to effect the oxidation. The reaction gas which leaves the reactor and contains the PA is precooled to 140°–180° C. and then passes into a separator system, in which the PA is separated out as a solid or liquid by further cooling of the reaction gas.

There are two variants of the process which differ in respect of the content of hydrocarbon in the vapor mixture with air. In one variant, a working pressure of more than 1 bar, and a hydrocarbon/air ratio which is generally above the lower explosive limit of hydrocarbon/air mixtures, are employed. Here, the oxidation is as a rule carried out in a fluidized bed and the PA is in the main separated out as liquid. For example, U.S. Pat. No. 3,535,345 describes a process which is carried out in a fluidized bed under 5.2–6.6 bar working pressure and with a hydrocarbon/air ratio of from 0.1 to 0.144:1, and which allegedly enables 90% of the PA to be separated out as liquid. A proportion of the compression energy, and the sensible heat in the exit gas are utilized by combusting the exit gas, after its enrichment with fuel gas, with air, and flashing the combustion gases in a gas turbine which in turn drives the process air compressor.

In the other process variant, which is usually a fixed bed process, the hydrocarbon/air ratio is kept below the explosive limit (for o-xylene/air this limit is 0.044 kg/m$^3$ (S.T.P.)) or above this limit. This process, which is operated under a pressure of less than 2 bar, does not allow liquid PA to be separated out, because the dew point is only reached after the temperature has fallen below the melting point of PA. This process requires substantially less compression energy, becaue the requisite process air pressure only depends on the pressure loss of the total installation. On the other hand, the separating-out of the PA is expensive, and the waste heat cannot be satisfactorily utilized. Usually, PA is separated out as a solid, by lowering the temperature of the gas, in a plurality of parallel separators which operate in a cooling/heating cycle, and is obtained as a liquid by melting the solid after switching over to heating operation. Heat removal during the cooling phase is via a heat transfer medium which is cooled again by exchange with the atmosphere, or directly via the cooling medium itself, for example water. Utilizatin of the heat to be removed is difficult, because the temperature profile of the gas to be cooled is too low to allow, for example, the use of evaporative cooling with the generation of saturated steam. Using the process air, before compression, as a cooling medium and compressing it when it is warm is ruled out by the compression energy required, which increases proportionately to the absolute temperature and in any case forms the main portion of the total energy consumption. After compression, the heated process air is no longer suitable for cooling purposes, particularly in summer operation.

We have found that PA can be produced particularly advantageously by catalytic oxidation of naphthalene or o-xylene with air, in which a preheated mixture of air and naphthalene or o-xylene is passed into a reactor charged with the catalyst, the reaction gas leaving the reactor then being passed through a separator in which the PA is separated out as a solid, if the air fed to the reactor is preheated, before or after the admixture of naphthalene or of o-xylene, by using it to cool the reaction gas in the PA separator.

The process according to the invention achieves a considerable improvement in waste heat utilization and energy balance in the industrial production of PA, and a substantial reduction in the investment component of the product costs, owing to the fact that a plurality of units as well as accessories, such as pipe runs and instrumentation, can be dispensed with.

In the novel process, the process air which is compressed to 1.4–1.7 bar, as is conventionally the case, is preheated to 125°–145° C. in a PA separator. The hydrocarbon is admixed beforehand or subsequently.

Accordingly, the process according to the invention dispenses with the conventional heating of the process air and of the hydrocarbon in separate preheaters and utilizes the waste heat of the PA separators for this preheating.

After this preheating, the hydrocarbon/air mixture is passed into the reactor. If separators in which the PA is separated out in solid form are used, the cooling action of the hydrocarbon/air mixture as a rule suffices to separate out the PA. If, during operation at temperatures prevailing at the height of summer, the injection cooling of the compressed air by the hydrocarbon alone does not suffice, the desired effect can be achieved by adding a hydrocarbon/water mixture, without thereby unacceptably raising the dew point of the exit gas downstream of the separator.

In the process according to the invention, mixtures of hydrocarbon and air in which the ratio of these components is below the lower explosive limit can be used to cool the reaction gases which leave the reactor zone and which are at from 140° to 180° C. Accordingly, suitable mixtures are those which contain not more than 40 g of naphthalene or 44 g of o-xylene per m$^3$ (S.T.P.) of air.

If the novel method is to be applied to a process for the preparation of PA in which a mixture of hydrocarbon and air having a ratio of these components above the lower explosive limit is passed into the reactor, it is advantageous to feed a non-explosive mixture of air and hydrocarbon into the solids separator and to bring this mixture to the desired ratio by introduction of additional hydrocarbon immediately upstream of the reactor. The transfer of the sensible heat from the PA-containing reaction gas, which is to be cooled, to the process air can also take place via an interposed heat transfer system, for example an oil circulation system.

EXAMPLE 1 (cf. FIG. 1)

Per hour, 56,000 m$^3$ (S.T.P.) of ambient air at 10° C. (annual mean temperature) are compressed to 1.513 bar in an air compressor. Per hour, 2,240 kg of o-xylene of commercial quality and 239 kg of water at 25° C. are injected at (4) into the compressed air, which is passed via a feed line (2) into the PA separator (3); this injection cools the mixture of air, o-xylene and water to 32° C. On flowing through the separator, the air/o-xylene mixture is heated to 135° C. As a result, an amount of useful heat of 1.922 million kcal per hour is removed from the reaction gas which is to be cooled in the separator (3) and which enters the latter, at 170° C., from the oxidation section (5) (which comprises the reactor, the waste heat boiler and the gas cooler) via the exit line (6). The residual heat is released into the atmosphere. The exit gas leaves the separator (3) through the exit line (7). The air/o-xylene mixture, which has been heated to 135° C. in the separator (3), passes into the reactor (5) via the line (8), a further 2,240 kg of o-xylene being added to the mixture per hour at (9).

In contrast to the conventional procedure (see Example 2), 1.922 million kcal of waste heat are utilized per hour. Assuming that boiler feed water at 152° C. was available, this would correspond to the additional production of 3.815 tonnes per hour of steam at 5 bar pressure.

Figure 2:
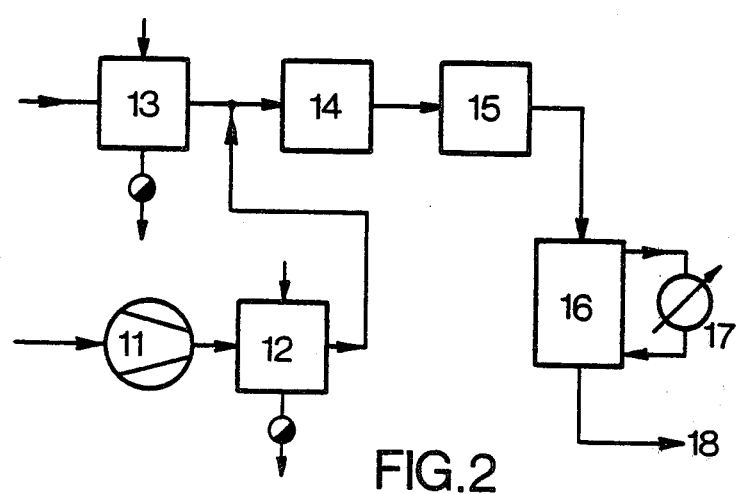

EXAMPLE 2 (Comparative Example) (cf. FIG. 2)

56,000 $m^3$ (S.T.P.) per hour of ambient air at 10° C. are compressed to 1.513 bar in an air compressor (11) and then preheated to 130° C. in a steam-heated heat exchanger (12). At the same time, 4,480 kg per hour of o-xylene of commercial quality are heated to 150° C. in a steam-heated heat exchanger (13). The o-xylene thus preheated is mixed with the preheated air and the mixture is passed into the oxidation unit (14), which comprises the reactor and the waste heat boiler. The PA-containing reaction gas, which leaves the oxidation unit (14) at 370° C., flows through the gas cooler (15), where it is cooled to about 170° C., saturated steam at 6 bar pressure being produced. The remaining heat to be removed is passed, in the PA separator (16), to a heat transfer medium circuit, and from the latter is released into the atmosphere in the air cooler (17). The exit gas leaves the separator (16) through the exit line (18).

We claim:

1. In a process for the preparation of phthalic anhydride (PA) by catalytic oxidation of a vaporized naphthalene or o-xylene with air at elevated temperatures and pressures, a preheated mixture of compressed air and naphthalene or o-xylene being passed into a reactor charged with the catalyst, and the reaction gas leaving the reactor being cooled to a temperature of 140° to 180° C. and then passed through a separator in which the PA is separated out as a solid, the improvement which comprises;
    preheating the air fed to the reactor, before or after the admixture of naphthalene or of o-xylene, by using it to cool the reaction gas in the PA separator, and
    cooling the feed air by introduction of the naphthalene or o-xylene with an injection cooling effect.

2. A process as claimed in claim 1, wherein the hydrocarbon content of the mixture of air and naphthalene or o-xylene which is heated in the PA separator by cooling the reaction gas is less than 40 g of naphthalene or 44 g of o-xylene per $m^3$ (S.T.P.) of air.

3. A process as claimed in claims 1 or 2, wherein the heat transfer from the reaction gas to the air to be fed to the reactor, or to the air/hydrocarbon mixture, is effected by means of a heat transfer system.

4. A process as claimed in claim 1 wherein said feed air is first compressed and then cooled by the introduction of naphthalene or o-xylene with an injection cooling effect in order to reduce its temperature sufficiently to act as a coolant for the reaction gas in said separator.

5. A process as claimed in claim 4 wherein said feed air is cooled by introduction of a mixture of water and said naphthalene or o-xylene to increase the injection cooling effect.

6. A process as claimed in claims 4 or 5 wherein the heat transfer from the reaction gas to the air/hydrocarbon mixture to be fed to the reactor is effected by means of a heat transfer system.